United States Patent
Romeas et al.

(10) Patent No.: US 6,314,313 B1
(45) Date of Patent: Nov. 6, 2001

(54) DEVICE AND PROCESS FOR SIMULATING A PATIENT'S BLOOD VESSELS

(75) Inventors: Rene Romeas, Palaiseau; Laurant Launay, Versailles; Yves Lucien Marie Trousset, Palaiseau; Regis Vaillant, Villebon sur Yvette, all of (FR)

(73) Assignee: GE Medical Systems S.A. (FR)

( * ) Notice: Subject to any disclaimer, the term of this patent is extended or adjusted under 35 U.S.C. 154(b) by 0 days.

(21) Appl. No.: 09/326,133

(22) Filed: Jun. 4, 1999

(30) Foreign Application Priority Data

Jun. 5, 1998 (FR) ................................... 98 07114

(51) Int. Cl.$^7$ ....................................... A61B 5/00
(52) U.S. Cl. ............................ 600/431; 378/18; 378/207
(58) Field of Search ..................................... 600/431, 416; 378/18, 208; 434/267, 268, 269, 272, 274, 218; 250/252.1, 496.1; 73/866.4

(56) References Cited

U.S. PATENT DOCUMENTS

| 4,400,827 | * | 8/1983 | Spears | 378/207 |
|---|---|---|---|---|
| 4,472,829 | * | 9/1984 | Riederer et al. | 378/207 |
| 4,618,978 | | 10/1986 | Cosman | 378/164 |
| 4,649,561 | | 3/1987 | Arnold et al. | 378/207 |
| 4,724,110 | * | 2/1988 | Arnold | 264/102 |
| 4,779,621 | * | 10/1988 | Mattson | 128/654 |
| 4,794,631 | | 12/1988 | Ridge | 378/207 |
| 4,985,906 | * | 1/1991 | Arnold | 378/18 |
| 5,376,803 | * | 12/1994 | Mc Fee et al. | 250/496.1 |
| 5,442,674 | | 8/1995 | Picard et al. | 378/20 |
| 5,465,720 | | 11/1995 | Kurzynski et al. | 128/660.01 |
| 5,712,895 | * | 1/1998 | Negrelli et al. | 378/207 |
| 5,719,916 | * | 2/1998 | Nelson et al. | 434/267 |
| 5,805,665 | * | 9/1998 | Nelson et al. | 378/207 |

FOREIGN PATENT DOCUMENTS

| 0527592 | 2/1993 | (EP) . |
|---|---|---|
| 9723164 | 7/1997 | (WO) . |

* cited by examiner

Primary Examiner—Marvin M. Lateef
Assistant Examiner—Eleni Mantis Mercader
(74) Attorney, Agent, or Firm—Jay L. Chaskin

(57) ABSTRACT

Device and process for simulating a patient's body for the testing of a three-dimensional vascular X-ray apparatus of the type comprising a means for emitting an X-ray beam, a means for receiving the X-ray beam, a means for displaying the images obtained, and a means for controlling the injection of opacifying liquid into the patient's vessels. The simulation device comprises a stationary part for simulating the patient's bones and soft tissues and a moving part for simulating the patient's opacified blood vessels, so as to be able to perform at least one acquisition of an image of the stationary part alone and at least one acquisition of an image of the stationary part and the moving part, and to obtain an image of the moving part by means of image.

13 Claims, 2 Drawing Sheets

DEVICE AND PROCESS FOR SIMULATING A PATIENT'S BLOOD VESSELS

This application claims the benefit of priority under 35 USC 112 of French Patent Application No. 98 07114 filed Jun. 5, 1998, the entire contents of which is hereby incorporated by reference.

BACKGROUND OF THE INVENTION

The present invention belongs to the field of devices that make it possible to simulate the body or a part of the body of a patient for the testing of an X-ray apparatus.

An X-ray apparatus generally comprises a tube that allows the emission of an X-ray beam in a given direction, means for positioning at least one part of a patient's body in the X-ray beam, and receiving means that sense the X-rays disposed in the beam after it has passed through the patient's body part. An X-ray apparatus requires the control of many parameters that can deviate over the course of time, which requires maintenance interventions at regular intervals. The reduction in the quality of the images obtained by the receiving means can be linked, for example, to slight changes in the geometry of the apparatus due to wear on the parts, or to variations in the magnetic field surrounding the apparatus.

In order to characterize such deviations, it is necessary to obtain a device that makes it possible to simulate the body of a patient. The display of the simulation device on a screen takes place in a way that is identical to that of the patient's body, and makes it possible to reveal possible deviations and thus to determine whether the X-ray apparatus is working with a precision greater than the minimal precision required or whether, on the contrary, the X-ray apparatus should undergo a maintenance operation in order to restore the precision of the images obtained.

Simulation devices of this type are particularly useful in the field of vascular imaging by image subtraction. The blood vessels of the human body being naturally transparent to X-rays, an image is first taken without the addition of an opacifying product, after which an opacfying product, for example iodine-based, is injected into the patient's blood, which makes the blood opaque to X-rays, then a second image is taken after the opacifying product has been properly distributed through the patient's vascular network. The two images or series of images obtained being numbered by electronic means, an image subtraction is then performed, making it possible to remove from the second image the organs visible in the first one, i.e., the organs naturally visible to X-rays such as the bones, etc.

To simulate the body or a part of the body of a patient, it is possible to use a network of flexible conduits through which water, which is quasi-transparent to X-rays, is first circulated in order to perform the first image acquisition, then through which water to which an opacifying product, generally iodine, is added before performing the second image acquisition. Next, the image substraction is performed in order to display the liquid circuit and to determine whether the X-ray apparatus is properly adjusted or, conversely, whether the image obtained has inconsistencies relative to the liquid circuit, whose geometry is known. However, a device of this type requires the utilization of a liquid, which complicates its handling. The iodine used as an opacifying product can cause bright spots, and it makes it necessary to wash the liquid circuit completely after its use. The handling of these simulation devices is therefore complicated, awkward, time-consuming and hence, costly.

BRIEF SUMMARY OF THE INVENTION

The present invention is a simulation device that is easy to handle and does not require any modification of the X-ray apparatus, while being adaptable to various types of X-ray apparatuses.

The device for simulating a patient's body provides for the testing of a vascular X-ray apparatus of the type comprising a means for emitting an X-ray beam, a means for receiving the X-ray beam, a means for displaying the images obtained, and a means for controlling the injection of opacifying liquid into the patient's vessels.

The simulation device comprises a stationary part for simulating the patient's bones and soft tissues and a moving part for simulating the patient's opacified blood vessels, so as to be able to perform at least one acquisition of an image of the stationary part alone and at least one acquisition of the image of the stationary part and the moving part together, and to obtain an image of the moving part by means of image subtraction. An important advantage of the simulation device is that it does not require the use of difficult-to-handle opacifying products, and that it can be used dry, without the use of water.

Advantageously, the simulation device comprises a means for moving the moving part between a position outside the X-ray beam and a position inside the X-ray beam. The moving means is preferably capable of being controlled by the means for controlling the injection of opacifying liquid. The moving means can comprise a pneumatic actuator, one end of which is integral with the stationary part and another end of which is integral with the moving part, a conduit for supplying air to the actuator, and a syringe connected to the supply conduit of the actuator. The syringe can be disposed inside the means for controlling the injection of the opacifying liquid into the patient's vessels.

Preferably, the syringe is filled with air at the atmospheric pressure.

In one embodiment of the invention, the stationary part has a hollow shape and is made of plexiglas. It can also be made of polycarbonate or any other material of comparable density.

In one embodiment of the invention, the moving part is disposed inside the stationary part and is made of a metal alloy on a plastic support.

The invention is a process for simulating a patient's body for the testing of a vascular X-ray apparatus of the type comprising a means for emitting an X-ray beam, a means for receiving the X-ray beam, a means for displaying the images obtained, and a means for controlling the injection of opacifying liquid into the patient's vessels, in which at least one acquisition of images of a stationary part for simulating the patient's bones and soft tissues and at least one acquisition of images of the stationary part and of a moving part for simulating the opacified blood vessels of the patient are performed, and an image of the moving part is obtained by means of image subtraction.

The simulation device can be controlled by the X-ray apparatus by installing an air-filled syringe into the means for controlling the injection of opacifying liquid. When the syringe is actuated, the air contained in it is forced into the conduit, then into a chamber of the pneumatic actuator, causing the moving part to move from one position to another position. A movement of the syringe in the opposite direction causes the stationary part to move in the opposite direction.

The simulation device can therefore be controlled by the X-ray apparatus without any modification of the latter, or any addition of electronic means that could be complex and costly.

BRIEF DESCRIPTION OF THE DRAWING

The present invention will be better understood through the study of the detailed description of an embodiment provided as a non-limiting example and illustrated by the attached drawings, in which.

DETAILED DESCRIPTION OF THE INVENTION

Figure 1:
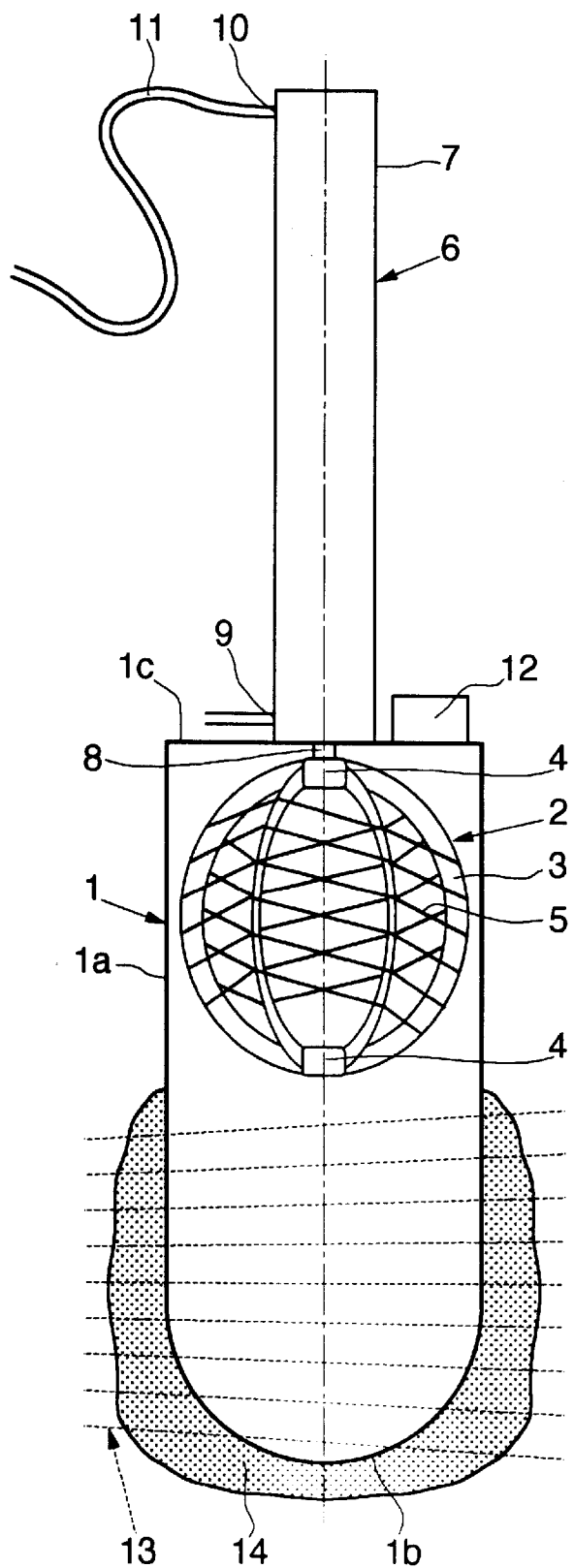
FIG. 1 is a schematic side elevation of a simulation device of one embodiment of the invention, the moving part being in a first position.

As may be seen in the figures, the simulation device comprises a hollow stationary part 1 made of plexiglas and equipped with a cylindrical lateral wall 1a, a rounded bottom wall 1b and a flat top wall 1c. Plexiglas is a material that makes it possible to simulate the soft tissues of a patient's body; other materials of higher density could be included in order to simulate the bones.

The simulation device comprises a moving part 2 made of metal alloy wires on a plastic support which is not very absorbent of the rays, having an approximately spherical shape and comprising semicircular members 3 extending from the bottom pole of the moving part 2 to the top pole. Provided at each pole is a supporting piece 4, to which the members 3 are attached. A network of metal wires 5 is attached around the members 3.

Disposed on the top wall 1c of the stationary part 1 is a pneumatic actuator 6 comprising a stationary element forming a cylinder 7, and a moving plunger rod 8 passing through the top wall 1c and integral with the supporting piece 4 of the top pole of the movable part 2. The actuator 6 can be single-acting or double-acting. As illustrated, the actuator 6 is double-acting and consequently has a bottom opening 9 and a top opening 10. However, the lower opening 9 is left open to the ambient atmosphere and only the bottom opening 10 is used. Thus, the actuator 6 behaves like a single-acting actuator. A flexible air conduit 11 is connected at one end to the bottom opening 10 of the actuator 6, and at another end, not represented, to a conventional type of syringe.

The stationary part 1 also comprises a mechanism 12 for equalizing the pressure between the inside of the stationary part 1 and the ambient atmosphere. The pressure equalizing mechanism 12 can exist in the form of a flexible membrane or a hole of very small diameter.

As seen in FIG. 1, the rod 8 is in the retracted position and the moving part 2 is in the top part of the fixed part 1. The X-ray beam 13 is represented by a plurality of dotted lines. It may be seen that the moving part 2 is outside the X-ray beam 13.

It may also be seen that the bottom part of the stationary part 1 is surrounded by an element 14. This element 14, whose presence is optional, makes it possible to better simulate the patient's bones and soft tissues by increasing the thickness of the matter through which the X-rays pass.

Figure 2:
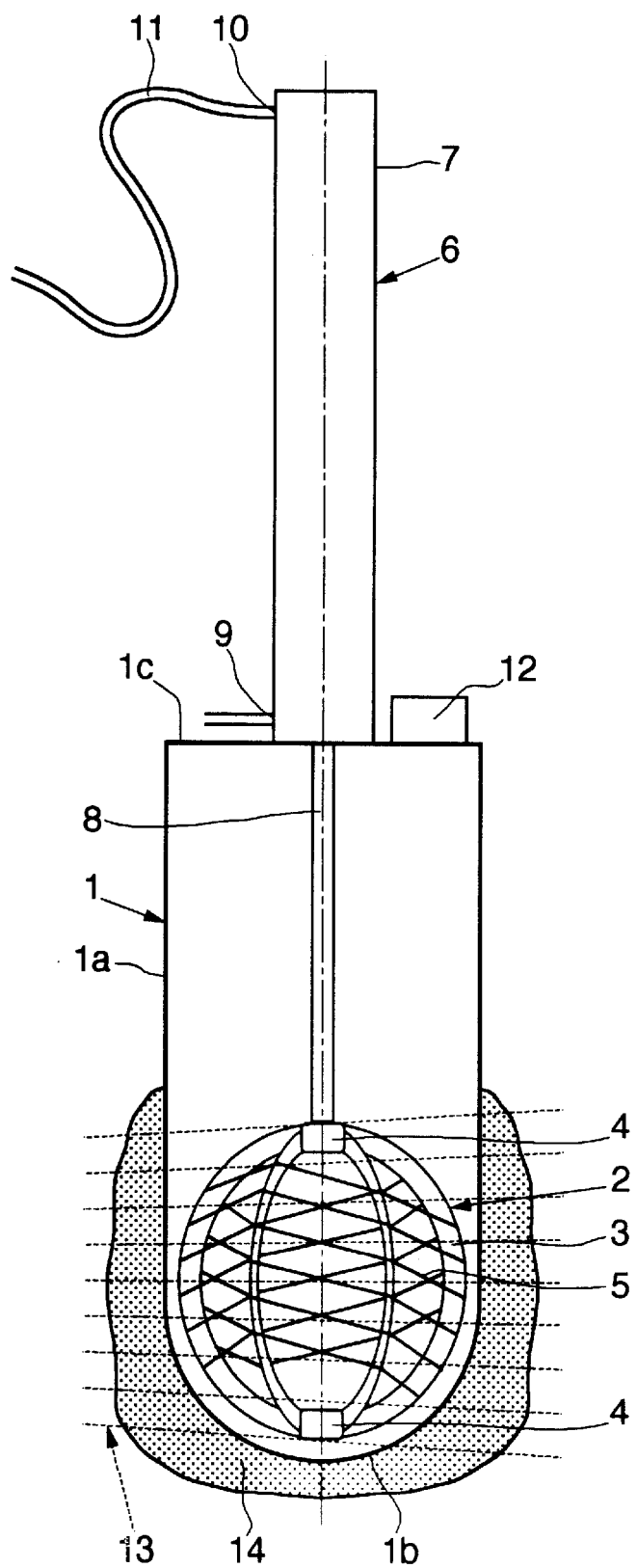
FIG. 2 is a view similar to FIG. 1, the moving part being in a second position.

When the simulation device is in the position of FIG. 1, a first image acquisition or a first series of image acquisitions is performed, which makes it possible to display the stationary part 1, possibly equipped with its element 14. Next, an operator actuates the syringe connected to the flexible conduit 11 by forcing out the air present in said syringe. This operation is preferably performed automatically. The air passes through the flexible conduit 11 into the cylinder 7 of the actuator 6 and tends to drive the rod 8, which causes the moving part 2 to move into the position illustrated in FIG. 2.

Thus, the moving part moves into the X-ray beam 13. It is then possible to perform a second image acquisition or series of image acquisitions, making it possible to display the stationary part 1, the moving part 2 and possibly the element 14. The images being numbered by computing means of the X-ray apparatus, not represented, an image subtraction operation is then performed, which makes it possible to retain a display of the moving part 2 only. The observation of the image of the movable part 2 thus obtained makes it possible to deduce whether the X-ray apparatus is properly calibrated or whether it should undergo a maintenance operation intended to return it to the desired precision. In effect, when the apparatus improperly calibrated, the image of the moving part 2 has a certain number of defects such as blurs, shape deformations, etc.

The conventional type of syringe that controls the movement of the actuator 6 is disposed in a part of the X-ray apparatus that is used to control and actuate the injection of opacifying liquid into the patient's bloodstream. This controlling and actuating part, comprises a syringe receptacle inside which the cylinder of the syringe can be easily locked, and an actuator that renders it integral with the plunger of the syringe so that said actuator can control the movement of the plunger of the syringe, and consequently control the movement of the moving part 2 of the simulation device.

This actuator is controlled automatically by electronic means of the X-ray apparatus, in order to perform the various image acquisitions without, then with, an opacifying product in the case of a patient, and with the moving part 2 in the upper position, then in the lower position, in the case of the simulation device. Thus, the simulation device can be controlled by existing elements of the X-ray apparatus without any modification of the latter.

The invention provides a device, also called a "phantom," for simulating a part of a patient's body, making it possible to test an X-ray apparatus with a simple operation, without handling an opacifying product, and, in general, without handling any liquid. However, it is also possible to fill the internal space of the stationary part 1 with a liquid (water) in order to better simulate the soft tissues that surround the blood vessels. In any case, the simulation is achieved as a result of the movement of a solid structure simulating the blood vessels.

Various modifications in structure and/or function and/or steps may be made by one skilled in the art to the disclosed embodiments without departing from the scope of the invention.

What is claimed is:

1. Device for simulating a patient's body for the testing of a vascular X-ray apparatus comprising means for emitting an X-ray beam, means for receiving the X-ray beam, means for displaying the images obtained, and means for controlling the injection of opacifying liquid into the patient's vessels, wherein the device comprises a stationary part for simulating the patient's bones and soft tissues, a structural member supported for movement relative to the stationary part and to the X-ray beam, for simulating the patient's opacified blood vessels, so as to be able to perform at least one acquisition of an image of the stationary part alone and at least one acquisition of an image of the stationary part and the structural member during movement and to obtain an image of the structural member during movement by means of image subtraction.

2. Device according to claim 1, comprising means for moving the structural member between a position outside the X-ray beam and a position inside the X-ray beam.

3. Device according to claim 2, wherein the moving means is capable of being controlled by the means for controlling the injection of opacifying liquid.

4. Device according to claim 3, wherein the moving means comprises a pneumatic actuator, one end of which is integral with the stationary part and another end of which is integral with the structural member, a conduit for supplying air to the actuator, and a syringe, also connected to the supply conduit of the actuator.

5. Device according to claim 4, wherein the syringe is disposed inside the means for controlling the injection of opacifying liquid into the patient's vessels.

6. Device according to claim 5, wherein the syringe is filled with air.

7. Device according to claim 1, wherein the stationary part has a hollow shape and is made of plexiglas, polycarbonate, or another material of comparable density.

8. Device according to claim 1, wherein the moving part is disposed inside the stationary part and is made of a metal alloy.

9. Process for simulating a patient's body for the testing of a vascular X-ray apparatus having means for emitting an X-ray beam, means for receiving the X-ray beam, means for displaying the images obtained, a movable member and means for controlling the injection of opacifying liquid into the patient's vessels, comprising the steps in which at least one acquisition of images of a stationary part for simulating the patient's bones and soft tissues and one acquisition of at least one image of a stationary part and of the movable member while it is being moved relative to the stationary part for simulating the patient's opacified blood vessels, and an image of the movable member is obtained by means of image subtraction.

10. Device for simulating a patient's body for the testing of a vascular X-ray apparatus comprising means for emitting an X-ray beam, means for receiving the X-ray beam, means for displaying the image obtained, and means for controlling the injection of opacifying liquid into the patient's vessels, wherein the device comprises a stationary part for simulating the patient's bones and soft tissues, a movable structural member for simulating the patient's opacified blood vessels and means for moving the structural member relative to the stationary member so as to be able to perform at least one acquisition of an image of the stationary part alone and at least one acquisition of a combined image of the stationary part and the movable structural member and to obtain an image of the structural member by means of image subtraction.

11. Device according to claim 10, wherein said structural member is moved along a linear axis from a position outside the X-ray beam and a position inside the X-ray beam.

12. Device according to claim 11, wherein said structural member comprises a plurality of wires arranged in a predetermined geometrical configuration.

13. Device according to claim 12, wherein said moving means comprises an actuator having a movable piston which is connected to said structural member.

\* \* \* \* \*